(12) United States Patent
Mezine et al.

(10) Patent No.: US 7,517,541 B2
(45) Date of Patent: Apr. 14, 2009

(54) **ORAL CARE COMPOSITIONS DERIVED FROM THE *LABIATAE* FAMILY**

(75) Inventors: Igor Mezine, Malvern, PA (US); Huizhen Zhang, Chalfont, PA (US); Mike Petteruti, Hilltown, PA (US); Mary Opet, Hopewell, NJ (US); John Finley, Lansdale, PA (US)

(73) Assignee: A.M. Todd Company, Montgomeryville, PA (US)

( * ) Notice: Subject to any disclaimer, the term of this patent is extended or adjusted under 35 U.S.C. 154(b) by 0 days.

(21) Appl. No.: 11/334,719

(22) Filed: Jan. 18, 2006

(65) Prior Publication Data

US 2006/0188589 A1    Aug. 24, 2006

Related U.S. Application Data

(60) Provisional application No. 60/644,738, filed on Jan. 18, 2005.

(51) Int. Cl.
A61K 36/534    (2006.01)

(52) U.S. Cl. .................................. 424/747; 424/401

(58) Field of Classification Search .................. None
See application file for complete search history.

(56) References Cited

U.S. PATENT DOCUMENTS

| | | | |
|---|---|---|---|
| 4,156,715 A | 5/1979 | Wagendnecht et al. | |
| 4,160,820 A | 7/1979 | Wagendnecht et al. | |
| 4,855,128 A | 8/1989 | Lynch et al. | |
| 5,002,759 A | 3/1991 | Gaffar et al. | |
| 5,043,153 A | 8/1991 | Videki et al. | |
| 5,204,089 A | 4/1993 | Hara et al. | |
| 5,240,704 A | 8/1993 | Tsurumizu et al. | |
| 5,310,542 A | 5/1994 | Au et al. | |
| 5,316,760 A | 5/1994 | Voerman | |
| 5,362,480 A | 11/1994 | Au et al. | |
| 5,409,692 A | 4/1995 | Nakahara et al. | |
| 5,439,680 A | 8/1995 | Horikoshi et al. | |
| 5,472,684 A | 12/1995 | Nabi et al. | |
| 5,490,978 A | 2/1996 | Spaltro et al. | |
| 5,683,678 A | 11/1997 | Heckert et al. | |
| 5,840,322 A | 11/1998 | Weiss et al. | |
| 5,853,728 A | 12/1998 | Tanabe et al. | |
| 5,858,992 A | 1/1999 | Nishimoto et al. | |
| 5,908,650 A | 6/1999 | Lenoble et al. | |
| 5,910,308 A | 6/1999 | D'Jang | |
| 5,939,050 A | 8/1999 | Iyer et al. | |
| 6,060,061 A | 5/2000 | Breton et al. | |
| 6,159,451 A | 12/2000 | Kim et al. | |
| 6,207,164 B1 | 3/2001 | Kreuter et al. | |
| 6,231,877 B1 | 5/2001 | Vacher et al. | |
| 6,303,125 B1 | 10/2001 | Ofek et al. | |
| 6,514,541 B2 | 2/2003 | Khanuja et al. | |
| 6,531,115 B1 | 3/2003 | Singh et al. | |
| 6,582,736 B2 | 6/2003 | Quezada | |
| 6,649,660 B2 | 11/2003 | Ninkov | |
| 6,689,342 B1 | 2/2004 | Pan et al. | |
| 6,869,624 B2 | 3/2005 | Maughan et al. | |
| 2002/0048611 A1 | 4/2002 | Ofek et al. | |
| 2003/0049303 A1 | 3/2003 | Ning et al. | |
| 2003/0138537 A1* | 7/2003 | Bailey et al. | ............. 426/542 |
| 2003/0175283 A1 | 9/2003 | Khanjua et al. | |
| 2003/0176393 A1 | 9/2003 | Koyama et al. | |
| 2003/0225003 A1 | 12/2003 | Ninkov | |

FOREIGN PATENT DOCUMENTS

| | | | |
|---|---|---|---|
| CH | 262262 | * | 9/1949 |
| HU | 210005 B | * | 7/1995 |

OTHER PUBLICATIONS http://dictionary.reference.com/browse/fresh—accessed Mar. 13, 2008.*

Kohlmunzer et al. (Herba Polonica (1975), vol. 21, No. 2, pp. 130-137).*

Lugasi et al. (Special Publication—Royal Society of Chemistry (1996), 179 (Agri-Food Quality), 372-375).*

Moreno L, Bello R, Primo-Yufera E, Esplugues J. Pharmacological properties of the methanol extract from *Mentha suaveolens* Ehrh. Phytother Res. Mar. 2002;16 Suppl 1:S10-3. (Abstract).

Villasenor IM, Angelada J, Canlas AP, Echegoyen D. Bioactivity studies on beta-sitosterol and its glucoside. *Phytother Res.* Aug. 2002;16(5):417-21. (Abstract).

Mimica-Dukic N, Bozin B, Sokovic M, Mihajlovic B, Matavulj M. Antimicrobial and antioxidant activities of three *Mentha* species essential oils. Planta Med. May 2003;69(5):413-9. (Abstract).

Aridogan BC, Baydar H, Kaya S, Demirci M, Ozbasar D, Mumcu E. Antimicrobial activity and chemical composition of some essential oils. Arch Pharm Res. Dec. 2002;25(6):860-4. (Abstract).

Iscan G, Kirimer N, Kurkcuoglu M, Baser KH, Demirci F. Antimicrobial screening of *Mentha piperita* essential oils. J Agric Food Chem. Jul. 3, 2002;50(14):3943-6. (Abstract).

Dorman HJ, Kosar M, Kahlos K, Holm Y, Hiltunen R. Antioxidant properties and composition of aqueous extracts from *Mentha* species, hybrids, varieties, and cultivars. J Agric Food Chem. Jul. 30, 2003;51(16):4563-9. (Abstract).

Zheng J, Wu LJ, Zheng L, Wu B, Song AH. Two new monoterpenoid glycosides from *Mentha spicata* L. J Asian Nat Prod Res. Mar. 2003;5(1):69-73. (Abstract).

Ruiz del Castillo ML, Santa-Maria G, Herraiz M, Blanch GP. A comparative study of the ability of different techniques to extract menthol from *Mentha piperita*. J Chromatogr Sci. Aug. 2003;41(7):385-9. (Abstract).

(Continued)

*Primary Examiner*—Susan C Hoffman
(74) *Attorney, Agent, or Firm*—Hueschen and Sage

(57) ABSTRACT

The invention relates to water dispersible extract preparations derived from water soluble components of *Labiatae* family plant material, including plant material hay and previously extracted or spent hay, which possesses beneficial oral care properties, methods of their manufacturing and application of the preparations in oral care products.

11 Claims, 18 Drawing Sheets

OTHER PUBLICATIONS

Shin TY. Inhibition of immunologic and nonimmunologic stimulation-mediated anaphylactic reactions by the aqueous extract of *Mentha arvensis*. Immunopharmacol Immunotoxicol. May 2003;25(2):273-83. (Abstract).

Zheng J, Zhao DS, Wu B, Wu LJ. [A study on chemical constituents in the herb of *Mentha spicata*] Zhongguo Zhong Yao Za Zhi. Oct. 2002;27(10):749-51. Chinese. (Abstract).

Oumzil H, Ghoulami S, Rhajaoui M, Ilidrissi A, Fkih-Tetouani S, Faid M, Benjouad A. Antibacterial and antifungal activity of essential oils of *Mentha suaveolens*. Phytother Res. Dec. 2002;16(8):727-31. (Abstract).

* cited by examiner

Size – exclusive high performance liquid chromatography of *Mentha* fractions.

Conditions: Column: TSK-Gel SW200 (Tosoh Corp.) 4.6 x 300 mm. Mobile phase: 50 mM $NaH_2PO_4$, pH was adjusted to 6.5 by KOH. The flow rate was 0.25 mL/min.

GC/MS of Natural Peppermint Oil.

Major Compounds in Natural Peppermint Oil:

| Retention Time (Min) | Compound |
|---|---|
| 8.86 | 1-Menthone |
| 9.25 | Menthofuran |
| 9.63 | 5-methyl-2-(1-methyl)-cyclohexanone |
| 9.88 | Beta-Bourbonene |
| 11.40 | Camphane |
| 11.88 | Caryophyllene |
| 12.41 | Neo-Menthol |
| 13.53 | L-(-)-Menthol |
| 14.51 | Germacreme-D |

GC/MS of Thymol and Carvacrol Standards.

| Retention Time (min) | Compounds |
|---|---|
| 23.99 | Thymol |
| 24.47 | Carvacrol |

GC/MS of *Mentha* Water Extract from Example 1.

GC/MS of *Mentha* Methanol Extract from Example 2.

Inhibition of GTF by M1 extracts prepared from three different *Mentha* varieties.

Inhibition of GTF by the MD1, MD2 and MD3 Fractions.

Anti-GTF activities of MD1 Fractions derived from two different *Mentha* varieties.

HPLC Profile of the M1 Fraction.

GTF Inhibitory Activity of the M1 Fraction. M1 was fractionated by Size-Exclusive Chromatography. The GTF inhibitory activity is depicted for each fraction which is designated according to the time of elution, in minutes (X-axis).

GTF inhibitory activity and Reverse Phase HPLC trace of the MD1 Fraction.

FIGURE 12.

Total Ion Current Chromatogram of the low molecular weight constituents of the M2 fraction and characterization of the constituents.

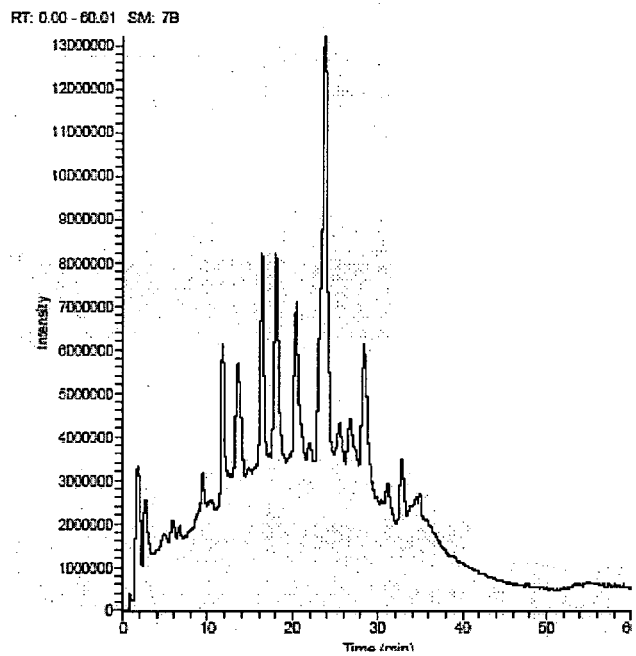

| RT, min | MS fragmentation pathway | Compound structure based on MS data |
|---|---|---|
| 4.6 | 359 -> 197 | Syringic acid derivative |
| 5.76 | 353 -> 191 | Chlorogenic acid |
| 8.48 | 341 -> 179 | Caffeic acid glucoside |
| 8.56 | 353 -> 191 | Caffeoylquinic acid 1 |
| 9.46 | 353 -> 191 | Caffeoylquinic acid 2 |
| 13.0 | 669 -> 595 -> 287 | Eriodictyol- (hexosyl-ramnosyl)-propionate |
| 13.25 | 623 -> 447 -> 285 | Luteolin glucoronide-hexoside |
| 14.49 | 637 -> 285 | Luteolin derivative |
| 14.5 | 469 -> 310 | Quercetin glucoronide |
| 16.46 | 595 -> 287 | Eriodictyol-7-O-rutinoside |
| 19.36 | 461 -> 285 | Luteolin glucoronide |
| 19.8 | 625 -> 579 -> 271 | Adduct:[naringenin-rutinoside +HCOOH-H]⁻ |
| 22.26 | 607 -> 299 -> 284 | Chrysoeriol rutinoside |
| 23.35 | 359 -> 161 -> 133 | Rosmarinic acid |
| 33.3 | 639 -> 593 -> 285 | Adduct: [Luteolin-rutinoside +HCOOH-H]⁻ |

Experimental set-up for determination of plaque accumulation on glass rods.

1-Reaction vessel; 2,3 – rubber cork with inserted glass rods; 4 – media reservoir; 5 – media inlet; 6 – three head peristaltic pump (P-3; Pharmacia) ; 7 – waste collector Glass rods following incubation.

Left side- Samples with inhibitor

Right side- Control samples, without inhibitor

INHIBITOR	CONTROL

Glass rods after drying.

Left side- Samples with inhibitor

Right side- Control samples, without inhibitor

INHIBITOR CONTROL

Changes in the calcium concentrations in mineralization solutions during the experiments.

Inhibition of cyclooxygenase 2 (COX-2) activity by water dispersible *Mentha* extract "M" preparations.

Inhibition of adhesion of *Streptococcus mutans* to Dextran.

ORAL CARE COMPOSITIONS DERIVED FROM THE *LABIATAE* FAMILY

FIELD OF THE INVENTION

Water dispersible extract preparations derived from water soluble components of Labiatae family plant material, including plant material hay and previously extracted or spent hay, which possess beneficial oral care properties, the methods of their manufacture and application of the preparations in oral care products.

BACKGROUND OF THE INVENTION

The botanical family known as Labiatae is commonly referred to as the mint family. Labiatae herbs include such genera as *Salvia* (sage), *Rosmarinus* (rosemary), *Mentha* (mint), *Ocimum* (basil), *Thymus* (thyme), *Marrubium* (hoarhound), *Monarda* (horse-mint), *Trichostema* (bluecurls), *Teucrium, Hyptis, Physostegia, Lamium* (henbit), *Stachys, Scutellaria* (skullcap), *Nepeta* (catmint). Members of the Verbenaceae family include *Lippia* (Mexican Oregano) and *Lycopus*.

Labiatae herbs are well known for the aromatic volatile or essential oils in their foliage, which oils are used in perfumes, flavorings, and medicines. Among the more important essential oils are those derived from sage, lavender, rosemary, patchouli, and the true mints. Members of the Labiatae family have been used for medicinal purposes, for example catnip, pennyroyal, hyssop, bee balm, yerba Buena and the true mints.

Typically, medicaments derived from members of family Labiatae utilize oil extracts from plants. In particular, antimicrobial compositions can be formulated by combining extracts of an essential oil with an organic acid or a Group I salt. It is believed that antimicrobial activity may be attributed to the presence of organic phenolic compounds, such as isopropyl-o-cresol, (5-isopropyl-2-methylphenol) and/or isopropyl-cresol (5-methyl-2[1-methylethyl]phenol) in the oil extract from the plants.

The natural compound menthol (essential oil alcohol) can be purified from the essential volatile oils of members of the *Mentha* genus. Menthol (1-Methyl-4-isopropyl cyclohexane-3-ol, or hexahydrothymol) is used in numerous products for its pleasing taste, aroma, and pharmacological properties. Menthol is known to have significant antibacterial activities and has been used in herbal treatments to cure internal and external infections.

Labiatae plants contain two other chemical compounds in their volatile oils which are known to possess antimicrobial activities. These are commonly referred to as carvacrol (5-isopropyl-2-methylphenol or isopropyl-o-cresol) and thymol (5-methyl-2[1-methylethyl]phenol or isopropyl-cresol). Both substances are monoterpene phenolic compounds and are potent antimicrobial agents. Typically, carvacrol and thymol can be synthetic or obtained from the oil extract of Labiatae plants.

Labaiate plants contain a number of phenolic compounds, such as eriocitrin, luteuolin-7 rutinoside, hesperoside, rosmarinic acid. (Duban F. et al., (1992) "*Aromatic and polyphenolic composition of infused peppermint, Mentha x. piperita L.*" Ann. Pharm. Fr. 50(3):146-55). The polyphenols are known to demonstrate antioxidant activity and are predominantly found in the aqueous or organic extracts of Labiatae plants.

Cells of *Mentha* plants are also known to contain a number of water-soluble polysaccharides, primary pectins, identified as (1-->3)-linked galactan carrying arabinosyl residues on C-6 and (1-->4)-alpha-linked galacturonan partially interspersed with (1-->2)-linked rhamnosyl residues (Maruyama K, et al., (1998) "*Pectins in extracellular polysaccharides from a cell-suspension culture of Mentha*"; Biosci Biotechnol Biochem. 62(11):2223-5). Other polysaccharide constituents are xyloglucans, containing xylose, glucose, arabinose, galactose, mannose and fucose residues. (Maruvama K, et al., (1996) "*O-acetylated xyloglucan in extracellular polysaccharides from cell-suspension cultures of Mentha.*" Phytochemistry 41(5): 1309-14).

Plants of the Labiatae family are highly valued for their essential oils. Components derived from the plant material, other than the essential oils, are also desired. Methods for isolating water soluble components from Labiatae plant materials are disclosed in U.S. Pat. No. 5,908,650 to Lenoble, et al. Lenoble, et al. describe a process of preparing a water-soluble rosemary extract by extracting rosemary leaves into water and acidifying the extract. The acidified crude extract is then loaded onto a reversed-phase media to remove undesirable components (e.g., polysaccharides, salts, and insoluble compounds). The desired fraction is then washed off the column. The isolated product contains a significant amount of flavonoid glucuronides and glycosides in addition to the antioxidant rosmarinic acid. Furthermore, the material isolated by the Lenoble, et al. method contains too much flavor and color to be suitable in certain applications.

A method of producing an improved water-soluble plant extract of one or more antioxidant compounds from Labiatae plant material is disclosed in Bailey, et al. (U.S. Published Patent Application No. 2003/0138537). The process disclosed in Bailey, et al. generally includes hot water extraction of the plant biomass for several hours, followed by acidification of the water extract and extraction of the antioxidant compounds into a water-immiscible organic solvent. Bailey, et al. describe an improved purification scheme for antioxidant compounds from Labiatae family plant material and is selective for the purification of antioxidants through acidification. Bailey, et al. discuss that a higher percentage of the desired antioxidant compound could be isolated by converting it to the protonated at low pH (below pKi) form and resulting in a higher percentage which is recovered in the water-immiscible organic solvent. The extract may be further processed to remove remaining trace amounts of compounds responsible for the taste, odor, and/or color which may be undesirable in certain commercial applications.

Commercial applications for Labiatae family plant extracts include the flavoring agents, flavor stabilizers, pigment stabilizing agents and antimicrobial agents. Labiatae-derived essential oils are used in dental care preparations primarily as flavoring agents and for the antimicrobial benefits afforded from the carvacrol and thymol components in the oils. As the Labiatae essential oils often impart strong organoleptic characteristics, it is desired to provide a composition for oral care which does not impart unwanted flavors in the oral care composition.

The aims of oral care are to prevent and/or treat dental diseases as well as provide cosmetic benefits.

Dental caries is an oral disease caused by bacterial pathogens and it affects hundreds of millions of people worldwide. The primary pathogens responsible for colonizing the oral cavity are the bacteria *Streptococcus mutans* and *Streptococcus sorbinus.*

Caries are understood to result from the accumulation of plaque on the teeth and production of organic acids (plaque acids) when plaque bacteria ferment sugars and starches in food residue left behind in the oral cavity. Before being washed away by saliva, the acids accumulate in the plaque long enough to lower the pH and to cause some of the enamel, a calcium-phosphorous mineral known as hydroxyapatite, to dissolve, that is, demineralize, which can lead to dental caries (tooth decay), and tooth sensitivity. Thus, the reversed process, re-mineralization, is an extremely important objective in the fields of preventive and restorative dentistry.

Another factor of cariogenesis is the accumulation of plaque bacteria which extracellularly produce glucosyltransferase (GTF) enzymes, which enzymes catalyze formation of glucans from sucrose. These glucans cover tooth surfaces and serve as the backbone of dental plaque. Plaque formation also involves the participation of a number of other opportunistic bacteria which are capable of attaching to the glucans and colonizing the tooth surface.

Glucosyltransferases are expressed and secreted by oral pathogens such as *Streptococcus mutans* and *Streptococcus sobrinus*. The GTF enzymes share a high degree of homology, and consist of two functional domains—catalytic and glucan binding, (Monchois V. et al, (1999) "*Glucansucrases: mechanism of action and structure-function relationships*" FEMS Microbiology Reviews 23:131-151). It is known that some low molecular weight inhibitors of GTF, such as 6-deoxysucrose, act through interfering with the catalytic domain of GTF. It is known that oligosaccharides or polysaccarides other than glucans can bind GTF and act as acceptors. To inhibit GTF activity, it may be desirable to obtain oligosaccharides or polysaccharides which are capable of binding with GTF, but are not able to serve as an acceptor for nascent glucan synthesis in plaque formation. Consequently, oral care preparations comprising such polysaccharides may be effective for preventing or reducing cariogenesis.

A method of preventing the formation or aggravation of dental plaque by inhibition of GTF activity is disclosed in U.S. Pat. No. 5,204,089 to Hara, et al. Inhibition of GTF activity is demonstrated with selected polyphenols derived from tea.

Inhibition of GTF activity by polyphenol compounds derived from the fruits of the Rosaceae family is disclosed in U.S. Pat. No. 5,853,728 to Tanabe, et al. The polyphenol derived from the fruits of Rosaceae family belongs to a group of plants having the highest free radical erasing activity among those reported for vegetable extracts evaluated. The polyphenol derived from the fruits of Rosaceae contains simple polyphenol compounds including caffeic acid derivatives, p-coumaric acid derivatives, flavan-3-ols, flavonols, dihydrochalcones, and condensed tannins. Polyphenols are disclosed to hinder the activity of glucosyltransferase produced by oral *Streptococcus*, specifically inhibiting the formation of deposit which is an important factor of dental caries. (Japanese Patent Application Laid-open No. 285876/1995). The disclosed function of the polyphenols also include antiallergic activity, ultraviolet light absorbing activity and free radical erasing activity for skin cosmetic material, and anticariogenic activity and deodorant activity for toothpaste.

Thus, a strategy for managing oral infections, besides mechanical removal of the formed plaque, may be based on application of antimicrobial agents, agents capable of inhibition of GTF, or their combination.

While there are a number of synthetic compounds on the market with anti-calculus properties, it is preferable that these agents be classified as "natural", or even more preferably, as "Generally Recognized as Safe" (GRAS). Various pharmaceuticals for inhibiting cariogenesis have been proposed; however, there is still a strong demand toward developing a pharmaceutical preparation which is unlikely to cause harmful side effects to the human body because it is derived from naturally occurring sources.

Associated with dental disease may be some form of inflammation at the tooth/gum interface. Inflammation or the inflammatory process is a natural result of an insult to soft tissue, usually resulting in vascular, cellulovascular and/or tissue fibrosis. Such physiological manifestation of inflammation has been attributed to the release of cytokines and other messengers such as serotonin, prostaglandins, bradykinin, leukotrienes, histamine, and substance P.

Inhibition of prostaglandin production is a mechanism which has been exploited in the treatment of inflammation. Typical inhibitors of prostaglandins include non-steroidal anti-inflammatory drugs (NSAIDs); however, these substances are not without side effects. NSAIDs are known to inhibit prostaglandin production by inhibiting enzymes in the arachidonic acid/prostaglandin pathway including, particularly, cyclooxygenase (COX). Recently, research has identified a cylcooxygenase subtype, COX-2, inhibition of which is highly effective in inhibiting inflammatory processes and which inhibition results in minimal untoward side effects. So-called COX-2 inhibition is therefore a popular target for treating/preventing inflammation, including inflammation associated with dental disease.

The Present Invention

The present invention is a water dispersible extract preparation derived from water soluble components of plant material of the Labiatae family and methods for obtaining such water dispersible fractions. Representative genera of the Labiatae herbs may include: *Salvia* (sage), *Rosmarinus* (rosemary), *Mentha* (mint), *Ocimum* (basil), *Thymus* (thyme), *Marrubium* (hoarhound), *Monarda* (horse-mint), *Trichostema* (bluecurls), *Teucrium, Hyptis, Physostegia, Lamium* (henbit), *Stachys, Scutellaria* (skullcap), *Nepeta* (catmint). Members of the Verbenaceae family include *Lippia* (Mexican Oregano) and *Lycopus*. Plant material comprises all parts of a plant, not limited to foliage, blossoms, stems, roots, and any other plant part. Moreover, this material may be fresh plant matter, plant matter which has been subjected to drying, steam distilling or other processes designed to remove the volatile essential oil components in the plant material.

The present invention encompasses a method for isolating water-dispersible components from Labiatae family plant biomass which demonstrate novel performance characteristics. The method of the present invention is different from the prior art processes for isolating antioxidants from plants of the Labiatae family. For example, the process of Lenoble, et al. is selective for the isolation of caffeic acid derivatives, flavonoid glycuronides and glycosides. Moreover, Lenoble, et al. eliminates undesired polysaccharide components from the extract through a column chromatography step.

The extraction method of the present invention results in a Labiatae plant extract which comprises a polyphenol component, a polysaccharide component, and optionally, a rosmarinic component. These methods of purification are distinct from the processes previously described as demonstrated by the composition of final products of the purification scheme. The extracts of the present invention which exhibit distinct constituents are responsible for the novel performance characteristics heretofore undisclosed for Labiatae family plant extracts.

Moreover, the present invention describes a method of providing beneficial oral care by means of preventing dental plaque accumulation, providing a remineralization effect, reducing inflammation in the oral cavity and providing a strong anti-oxidative capacity. These described effects may be achieved by contacting the oral cavity with products containing effective amounts of preparations derived from water soluble components of plant material of genera of the Labiatae family, in particular of the *Mentha* genus.

OBJECTS OF THE INVENTION

It is an object of the present invention to provide novel oral care compositions which are extract preparations derived from the water soluble components of plants of genera of the Labiatae family, in particular of the *Mentha* genus. It is a further object of the invention to provide a novel method of providing beneficial oral care by means of preventing dental plaque accumulation, providing a remineralization effect, reducing inflammation in the oral cavity and providing a strong anti-oxidative capacity.

SUMMARY OF THE INVENTION

What we therefore believe to be comprised by our invention may be summarized inter alia in the following words:

A water dispersible extract preparation of Labiatae family plant material comprising a polysaccharide component, a polyphenol component, and, optionally, a rosmarinic acid component, such a water dispersible extract preparation, comprising a polysaccharide component between 5% and 95%, a polyphenol component between 5% and 95%, and optionally, a rosmarinic acid component between 0% and 12% of the total mass, such a water dispersible extract preparation, comprising a polysaccharide component between 75% and 80%, a polyphenol component between 5% and 10% of the total mass, and which is substantially free of a rosmarinic acid component, such a water dispersible extract preparation, in which the preparation is substantially free of essential oil components, such a water dispersible extract preparation, in which the preparation is substantially free of thymol, menthol, and/or carvacrol components, such a water dispersible extract preparation, wherein the plant material is *Mentha* genus plant material, such a water dispersible extract preparation, wherein the *Mentha* plant material is derived from spent mint hay, such a water dispersible extract preparation, wherein the *Mentha* plant material is derived from spent mint hay which is dried, such a water dispersible extract preparation, wherein the *Mentha* plant material is derived from fresh mint hay, such a water dispersible extract preparation, wherein the *Mentha* plant material is derived from fresh mint hay which is dried, such a water dispersible extract preparation, further comprising extracts, fractions, and compounds possessing beneficial oral care properties including inhibitory activity towards to glucosyltransferases, remineralization properties, anti-adhesion activity, inhibitory activity towards cyclooxygenases and lipoxygenases, anti-oxidant properties, and/or anti-inflammatory properties, such a method of providing oral care benefits in a living animal, including a human, by means of inhibiting glucosyltransferases, inhibiting adhesion of oral pathogens and/or providing a remineralization effect, comprising the step of administering to the oral cavity of a living animal, including a human, an amount of a water dispersible extract preparation which is effective to provide an oral care benefit, such a method wherein the water dispersible extract preparation is selected for its inhibitory activity towards glucosyltransferases, anti-adhesion activity, remineralization properties and/or anti-inflammatory properties, such a method wherein the water dispersible extract preparation is contacted with the oral cavity in the form of a chewing gum, a breath freshening strip, a confectionary product, a food product, a beverage, a toothpaste/dentifrice, a mouthwash/rinse or a floss, pet food, pet snack, and pet chewing material, selected from pig's ears and raw hides, such a method wherein the beneficial effect of the water dispersible extract preparation may be further enhanced by incorporation of extracts, fractions, and compounds possessing beneficial oral care properties including inhibitory activity towards to glucosyltransferases, anti-microbial activity against oral pathogens, remineralization properties, anti-adhesion activity, inhibitory activity towards cyclooxygenases and lipoxygenases, breath freshening properties, anti-oxidant properties, and/or anti-inflammatory properties, such a method of providing a remineralization effect in a living animal, including a human comprising the step of administering to the oral cavity of living animal, including a human, an amount of a water dispersible extract preparation which is effective to provide a remineralization effect, such a process of manufacturing a water dispersable Labiatae extract preparation comprising a. contacting Labiatae plant material with water-organic mixtures:
   i. wherein a water-miscible organic solvent is selected from C1-C4 alcohols, acetone, and/or their combination,
   ii. wherein the pH of the water and/or water/organic solvent mixture is kept in the range 1-14 by means of appropriate base, acid, salt or buffer,
   iii. wherein the ratio of water to organic solvents is in a range from 100:0 to 1:99,
   iv. wherein the extraction is carried out at temperatures in a range from 0° C. to at boiling point;
   v. wherein the extraction may include microwave assisted water extractions and/or subcritical extraction with water, including high temperature and high pressure;
b. removing the extract from insoluble material;
c. optionally repeating the extraction step using the same or different water-organic mixture;
d. optional fractionation of the extracted material by means of precipitation
   i. wherein precipitation is achieved by increasing the content of the organic solvent chosen from C1-C4 alcohols, acetone, and/or their combination,
   ii. wherein precipitation is achieved by decreasing pH,
   iii. wherein precipitation is achieved through complexation with multicharged cations,
   iv. wherein precipitation is achieved by increasing ionic strength of the solution, and/or
   v. wherein precipitation is further aided by decreasing the temperature;
e. optional purification of the extracts by means of liquid—liquid extraction, solid-phase extraction, chromatographic methods, membrane-based filtration or combinations of thereof; and
f. stabilizing the obtained preparations by means of addition of anti-spoiling agents, or preferably by vacuum drying, or spray drying methods using appropriate carriers, such a process wherein the water dispersible Labiatae preparation is substantially free of thymol, menthol, and carvacrol, such a process wherein the pH of the water is kept in the range of 4 to 8, such a process wherein the pH of the water is kept in the range of 5 to 7, such a process wherein the extraction is carried out at a temperature of about 100° C., such a process wherein the ratio of water to organic solvents is 100:0, such a process wherein the ratio of water to organic solvents is in a range from 90:10 to 99:1 and wherein the extraction is carried out at temperatures in a range from 60° C. to 100° C., such a process wherein the ratio of water to organic solvents is in a range from 90:10 to 99:1 and wherein the extraction is carried out at temperatures in a range from 96° C. to 100° C., such a process wherein the organic solvent is ethanol, such a process wherein the ratio of water to ethanol is 1:1, such a process wherein the extraction includes microwave assisted water extractions and/or subcritical extraction with water, including high temperature and high pressure, such a process wherein the extracted material is fractionated by means of precipitation, such a process Wherein the extract is purified by means of liquid-liquid extraction, solid-phase extraction, chromatographic methods, membrane-based filtration and/or combinations of thereof, such a process wherein the Labiatae plant material is from a *Mentha* genus, such a process wherein the plant material of the *Mentha* genus is from "spent mint hay" which currently has been designated as waste stream resulting from the production of commercial "mint oil" or mint essential oil.

BRIEF DESCRIPTION OF THE FIGURES

FIG. 12 shows a Total Ion Current Chromatogram of the low molecular weight constituents of the M2 fraction and characterization of constituents. Separation was performed on a Hypersil Gold® C18 column using a gradient of acetonitrile in water (with formic acid). The eluent was analyzed using an LTQ liner ion trap equipped with an electrospray source operating in negative mode. LTQ was set to operate using data-dependent acquisition.

DETAILED DESCRIPTION OF THE INVENTION

Figure 1:
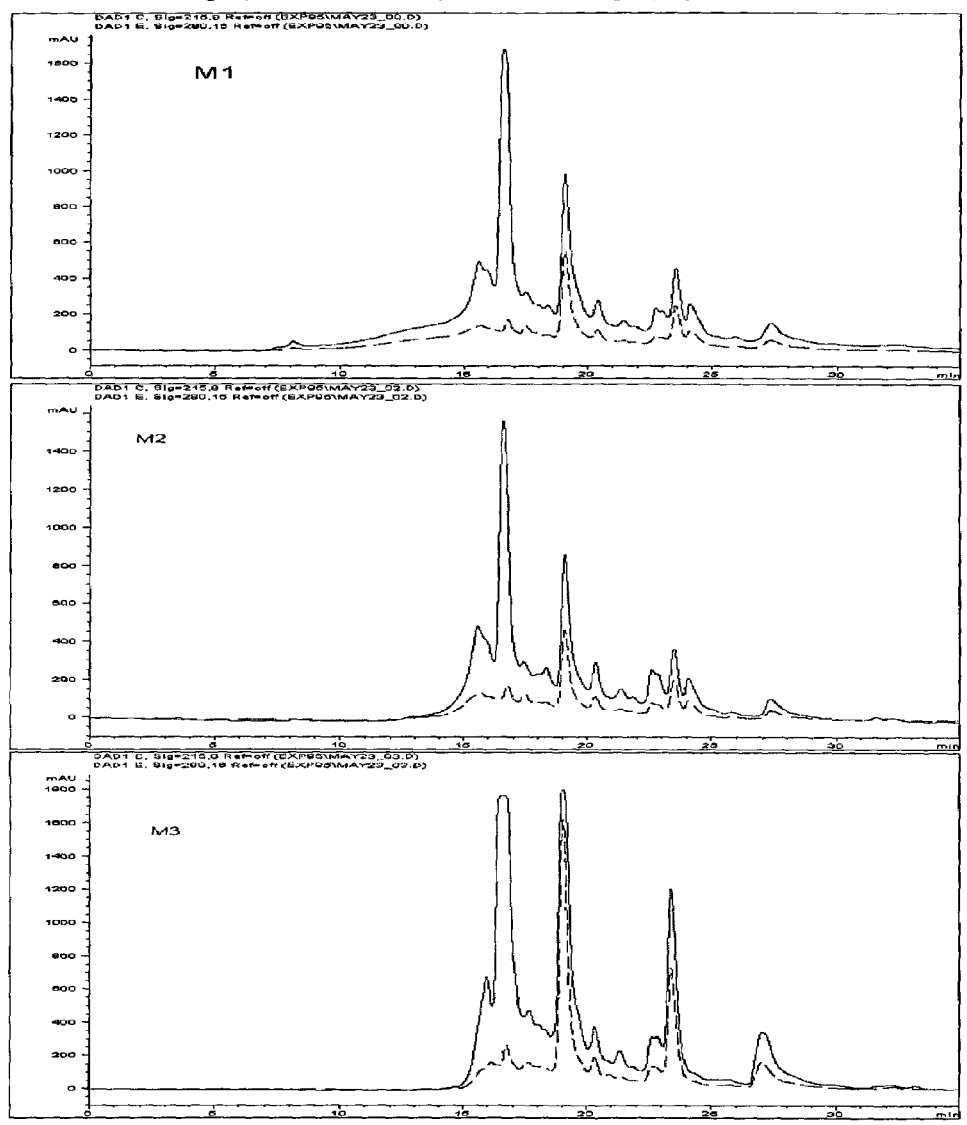
FIG. 1 shows HPLC chromatograms of *Mentha* fractions M1-M3 obtained as described in Example 1.
Figure 2:
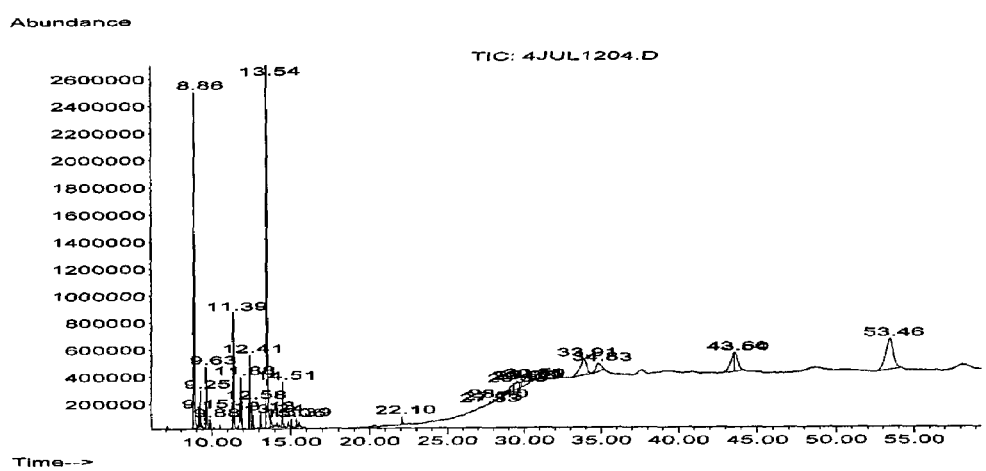
FIG. 2 shows a GC/MS chromatogram of Natural Peppermint Oil.
Figure 3:
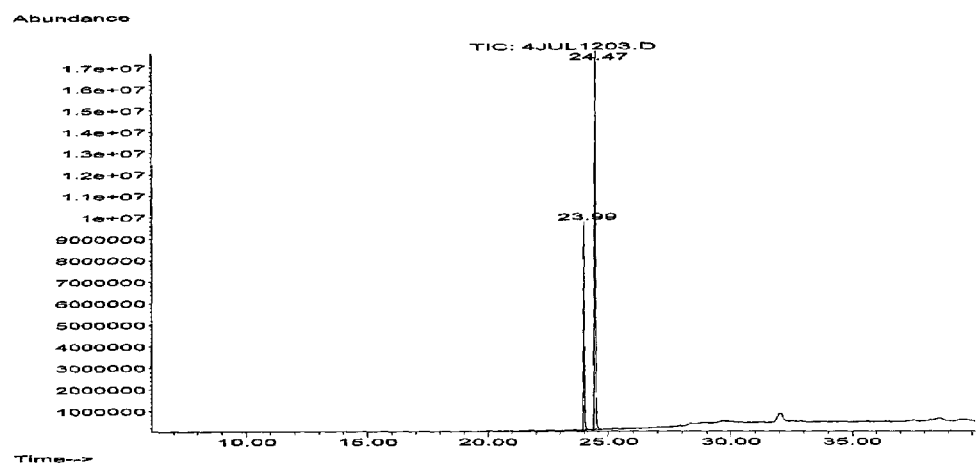
FIG. 3 shows a GC/MS chromatogram of Thymol and Carvacrol.
Figure 4:
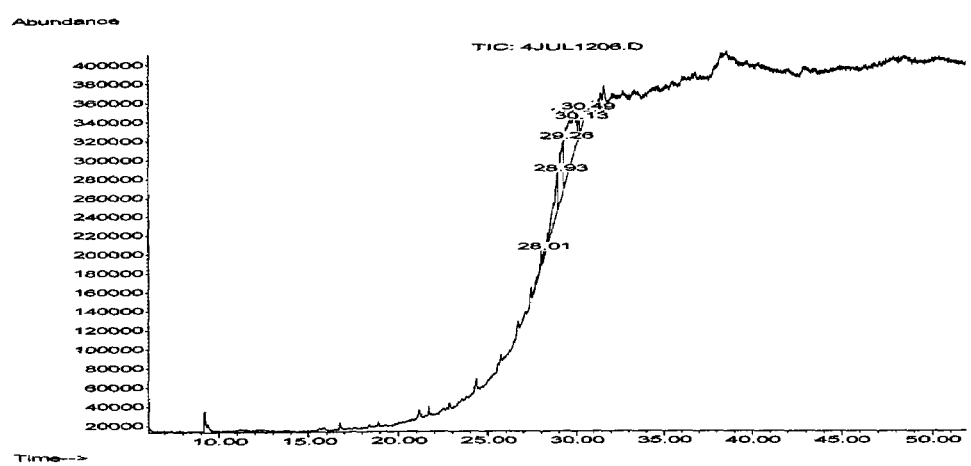
FIG. 4 shows a GC/MS chromatogram of the *Mentha* water extract, fraction M, obtained in Example 1.
Figure 5:
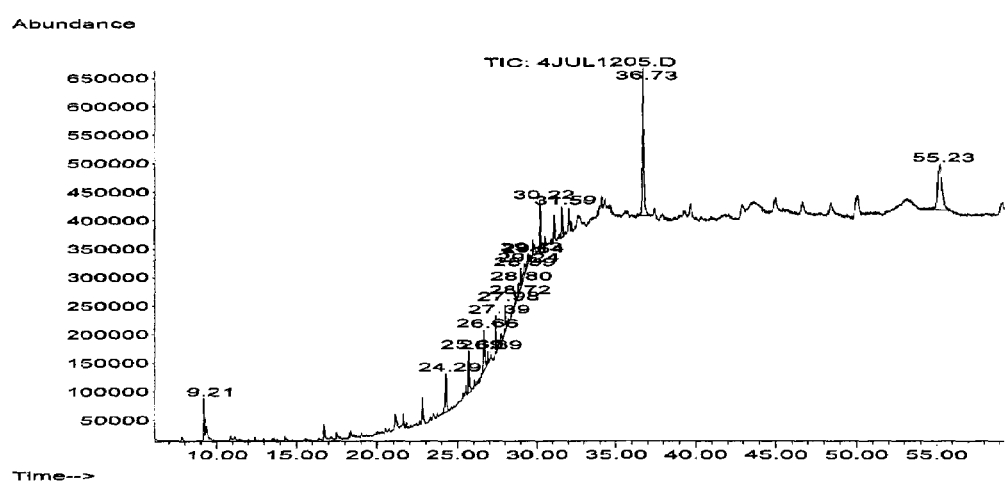
FIG. 5 shows a GC/MS chromatogram of a *Mentha* methanol extract obtained in Example 2.

The water dispersible extract preparations of the present invention will be better understood in connection with the following examples, which are intended as an illustration of and not a limitation upon the scope of the invention.

EXAMPLE 1

Extraction and Fractionation of Plants of *Mentha* Genus Using Previously Extracted Plant Material.

Processed peppermint leaves (600 g) were ground and extracted with boiling water (6.6 L) for 1 hour. After cooling, the extract was filtered. The pH, which ranged from approximately pH 4 to near neutrality, was not chemically altered from the native value during the extraction process. The water was evaporated from the filtered solution to obtain a black, semi-crystal material (150 g; yield 25%) and is referred to as the "M" fraction. This total extract was dissolved in water (600 mL), followed by the addition of 600 mL of a water-miscible organic solvent, such as MeOH, EtOH, acetone, and/or their combination. After addition of the organic solvent, the mixture was allowed to stand at room temperature for 2 hours to allow the formation of a precipitate. This material which was insoluble in 50% organic solvent, was filtered to yield a dark brown paste-like material (dry weight 37.4 g; yield 6.2%). Drying of this sample on high vacuum afforded a fraction referred to as "M1", which is a brown powder. The material which was soluble in 50% organic solvent was isolated by evaporation of the organic solvent to a minimal volume (to obtain: 140 g as a very viscous liquid) and then treated with organic solvent (700 mL; to a final concentration of about 95%) The material which was insoluble (in 95% organic solvent) was filtered and dried. This fraction, referred to as "M2", was a light brown powder (100 g, yield 17%). The material which was soluble in 95% organic solvent was isolated after evaporation of the organic solvent. This fraction is referred to as "M3", and was obtained as a dark brown, semi-solid material (12.0 g; yield 2.0%). After drying, the "M3" was obtained as a brown powder.

An analytical characterization of obtained fractions is presented in Table 1 and FIG. 1. The fractions were analyzed for total polysaccharide content, total polyphenol content (Table 1) and profiled using high performance liquid chromatography (FIG. 1).

TABLE 1

Analytical Characterization of *Mentha* genus Extracted Plant Material

|  | M | M1 | M2 |
|---|---|---|---|
| Total polyphenols (%) | 28.1 | 17.4 | 23.5 |
| Total polysaccharides (%) | 29.0 | 20.0 | 29.9 |
| Anti oxidant (ORAC) value | 1753 | 979 | 2316 |

EXAMPLE 2

Extraction of Plants of *Mentha* Genus Using Previously Extracted Plant Material.

Processed peppermint leaves (260 g) were extracted with boiling methanol (2.5 L) for 4 hours and the mixture was left at room temperature for another 20 hours. After 24 hours of total extraction time, the mixture was filtered to yield 1.5 L of dark green methanolic solution. Evaporation afforded 28 g of black-greenish semisolid material (1.1% yield).

EXAMPLE 3

GC/MS Analysis (for Mint Oil Related Compounds as Well as Thymol and Carvacrol) of Spent Mint Water Extracts and Spent Mint Methanol Extracts.

Analysis of the extracts obtained in Examples 1 and 2 was performed using GC (model 6890) hosted HP-Innowax capillary column (30 m×0.25 μM) interfaced with an MS detector (5973) (all from Agilent). The initial temperature was 30° C. (6 min), followed by ramping 6° C./min to a final temperature of 220° C. (hold for 30 min). The eluted peaks were identified by their mass spectra using reference standards. FIGS. 2-5 show that there were no mint oil related compounds, thymol, or carvacrol detected in the extracts obtained in Examples 1 and 2.

EXAMPLE 4

Fractionation of the Total Mint Hay Extract on Reversed Phase Resin Diaion® HP-20.

An extract of Example 1 (4 g) was dissolved in water (20 mL) and the obtained material was applied on a column packed with resin (22×4 cm). The column was pre-washed with MeOH, 50% MeOH and equilibrated with water (2 L). The material, MD1, MD2 or MD3, was then successively eluted with water (700 mL) to yield MD1, 50% MeOH (700 mL) to yield MD2, and 100% MeOH (700 mL) to yield MD3.

The Labiatae plant extract preparations and/or fractions which were isolated according to the aforementioned Examples were characterized. The composition of individual preparations/fractions is shown in Table 2. The elemental analysis of three fractions is provided in Table 3.

Characterization of Spent Mint Hay Fractions

Total Soluble Polysaccharides, Total Polyphenols and Rosmarinic Acid in Spent Mint Hay Fractions Samples:
1. M-03162004: Direct water extract from spent mint hay
2. M-03182004W: Direct water extract from spent mint hay
3. M-Exp123: Direct water extract from spent mint hay
4. M-03182004M: Direct water extract from spent mint hay
5. MD1-03102004: 100% water fraction of M from column packed with Diaion resin
6. MD1-03092004: 100% water fraction of M from column packed with Diaion resin
7. MD2-03102004: 50% methanol fraction of M from column packed with Diaion resin
8. MD2-03092004: 50% methanol fraction of M from column packed with Diaion resin
9. MD3-03102004: 100% methanol fraction of M from column packed with Diaion resin
10. MD3-03092004: 100% methanol fraction of M from column packed with Diaion resin
11. M1-03112004: 50% methanol insoluble fraction of M
12. M1-03172004E: 50% methanol insoluble fraction of M
13. M1-03172004M: 50% methanol insoluble fraction of M
14. M2-03112004: 50% methanol soluble fraction of M
15. M2-03172004E: 50% methanol soluble fraction of M
16. M2-03172004M: 50% methanol soluble fraction of M
17. M1A20_06102004: 20% methanol insoluble fraction of M
18. M1A40_06102004: 40% methanol insoluble fraction from sample 2
19. M1A60_06102004: 60% methanol insoluble fraction from sample 3
20. M1B40_06102004: 40% methanol insoluble fraction from M
21. M1C60_06102004: 60% methanol insoluble fraction of M
22. Methanol extract direct from spent mint hay
23. Exp127, HPLC MD1, Fraction #2
24. Exp127, HPLC MD1, Fraction #3
25. Exp127, HPLC MD1, Fraction #5
26. Exp127, HPLC MD1, Fraction #6
27. Fraction from Size-Exclusive chromatography of fraction M1: molecular weight ≧400 kDa.

TABLE 2

| | Testing Results (%): | | |
|---|---|---|---|
| Sample ID | Total Polysaccharides (%) | Total Polyphenols (%) | Rosmarinic Acid (%) |
| 1 | 19.9 | 34.8 | 1.3 |
| 2 | 16.1 | 38.0 | 1.1 |
| 3 | 17.6 | 33.1 | 1.4 |
| 4 | 25.5 | 27.2 | 2.6 |
| 5 | 20.7 | 7.2 | ND |
| 6 | 24.9 | 6.4 | ND |
| 7 | 9.9 | 74.8 | 5.0 |
| 8 | 10.2 | 73.6 | 5.1 |
| 9 | 25.4 | 58.2 | 0.4 |
| 10 | 18.7 | 58.0 | 0.3 |
| 11 | 18.8 | 31.0 | 1.0 |
| 12 | 17.9 | 30.2 | 0.7 |
| 13 | 14.8 | 34.7 | 0.9 |

TABLE 2-continued

Testing Results (%):

| Sample ID | Total Polysaccharides (%) | Total Polyphenols (%) | Rosmarinic Acid (%) |
|---|---|---|---|
| 14 | 24.3 | 33.7 | 1.7 |
| 15 | 14.9 | 40.8 | 1.5 |
| 16 | 21.8 | 39.5 | 1.5 |
| 17 | 18.4 | 24.3 | 0.75 |
| 18 | 20.8 | 30.7 | 0.73 |
| 19 | 22.9 | 31.0 | 0.67 |
| 20 | 24.4 | 25.4 | 0.70 |
| 21 | 23.1 | 28.1 | 0.76 |
| 22 | 21.7 | 27.0 | 2.60 |
| 23 | 4.0 | 2.5 | nd |
| 24 | 14.1 | 1.7 | nd |
| 25 | 48.2 | 12.2 | nd |
| 26 | 14.5 | 5.0 | nd |
| 27 | 75 | 18 | nd | nd = not detected

TABLE 3

Elemental Analyses of Spent Mint Hay Fractions

| Fraction | % C | % H | % N | % K | % Na | % Ca | % P | % S | % Mg | ppm Cu | ppm Fe | ppm Zn |
|---|---|---|---|---|---|---|---|---|---|---|---|---|
| M | 36.70 | 4.91 | 1.72 | 7.50 | 0.18 | 1.20 | 0.57 | 0.64 | 0.79 | 26 | 131 | 37 |
| M1 | 36.32 | 4.50 | 1.63 | 4.80 | 0.16 | | | | | | | |
| MD1 | 28.70 | 4.49 | 1.82 | 12.92 | 0.97 | | | | | | | |

EXAMPLE 5

Extraction and Fractionation of Plants of *Mentha* Genus Using Fresh Plant Material.

Fresh peppermint leaves (600 g) are ground and extracted with boiling water (6.6 L) for 1 hour. After cooling, the extract is filtered and the solution is evaporated. The resulting extract is dissolved in water (600 mL), followed by the addition of a water-miscible organic solvent (600 mL). After addition of the organic solvent, the mixture is allowed to stand at room temperature for 2 hours to allow the formation of precipitate. The insoluble material in 50% organic solvent is filtered and dried under high vacuum. The material soluble in 50% organic solvent is evaporated to a minimal volume and then is treated with organic solvent (700 mL) to obtain a solution comprising 95% organic solvent. The material which is insoluble in 95% organic solvent is filtered and dried. The material which is soluble in 95% organic solvent is then evaporated to yield a semi-solid material.

EXAMPLE 6

Separation and Characterization of *Mentha* Extractions and Anti-Glucosyltransferase (GTF) Activity of the Obtained Fractions.

Inhibition of GTF was evaluated based on measurement of incorporation of radioactive glucose, which is derived from [$^{14}$C]-labeled sucrose, into insoluble glucans, with and without the presence of the *Mentha* preparations.

The GTF used in the assay was purified from a culture of *Streptococcus sobrinus* to apparent homogeneity as observed upon SDS-PAGE. All reagents and enzymes are dissolved in 50 mM potassium-phosphate buffer (pH 6.5) containing sodium azide as a preservative (0.02%). The reaction was carried out in a 96-well polypropylene block (Corning).

The typical procedure was as follows: to a solution of a tested compound or blank (80 μL) in a well, an aliquot (20 μL) of the GTF solution (c=11 μg/mL) was added, immediately followed by addition of a solution containing sucrose (0.625 mg/mL) and uniformly [$^{14}$C]-labeled sucrose (80,000-90,000 CPM; NEN Company). The sampling block was sealed, placed in water bath (37° C.) and gently shaken for 2 hours. After incubation, the block was put on an ice bath, and the well content was transferred into a 96 well filtering plate (1 μm, glass fiber, Millipore). The insoluble glucans were filtered, the reaction wells were washed with water (2×200 μL), and the washing solution was transferred to the filtering plate again. After drying the filters were punched into scintillation vials, scintillation cocktail was added, and radioactivity was measured using a Packard counter.

Figure 6:
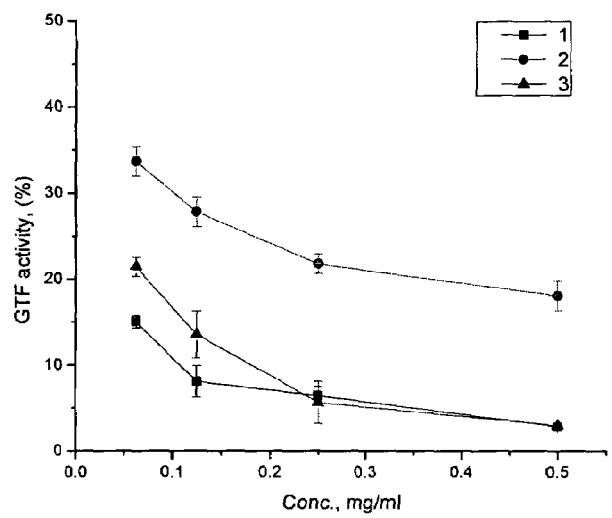
FIG. 6 shows the GTF inhibitory activity of three "M1" preparations which were isolated as described in Example 1, and were derived from three different *Mentha* varieties. GTF inhibition was determined as described in Example 6.
Figure 7:
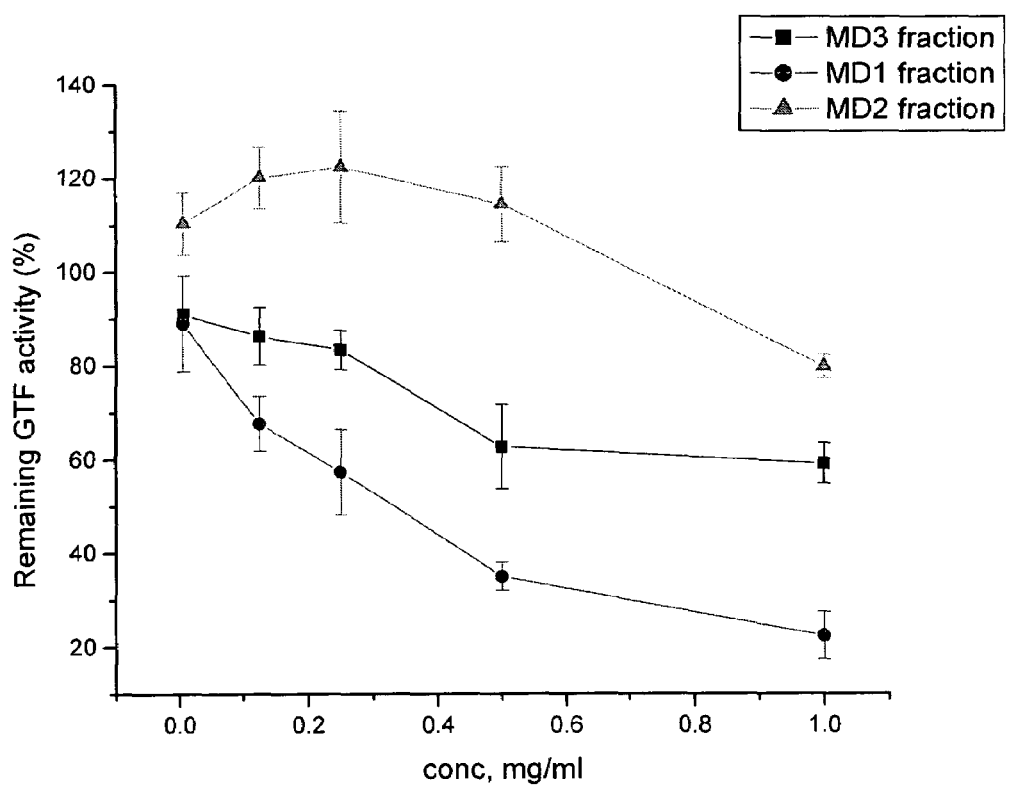
FIG. 7 shows GTF inhibitory activity, determined as described in Example 6, of fractions MD1, MD2 and MD3 which were isolated as described in Example 4.
Figure 8:
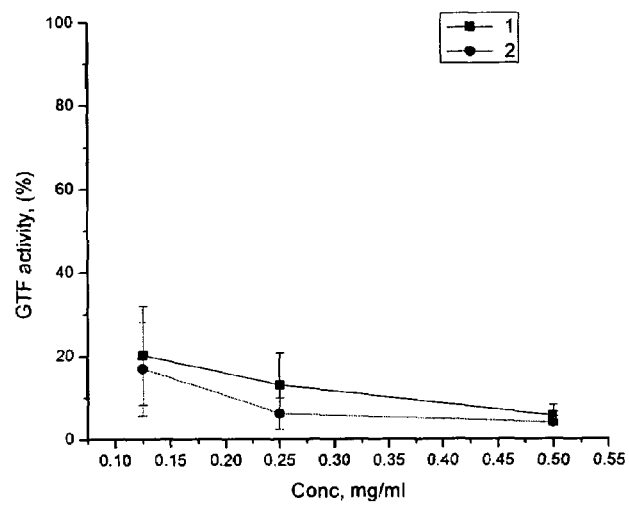
FIG. 8 shows GTF inhibitory activity of two MD1 fractions which were isolated as described in Example 4 and derived from two different *Mentha* varieties. GTF inhibition was determined as described in Example 6.

GTF inhibitory activity of several *Mentha* preparations is shown in FIGS. 6-8. FIG. 6 shows GTF inhibitory activity of the "M1" fraction derived from different *Mentha* varieties, which were isolated as described in Example 1. FIG. 7 shows GTF inhibitory activity of fractions MD1, MD2 and MD3, which were isolated as described in Example 4. FIG. 8 shows GTF inhibitory activity of two MD1 fractions, which were isolated from two different *Mentha* varieties as described in Example 4.

Figure 9:
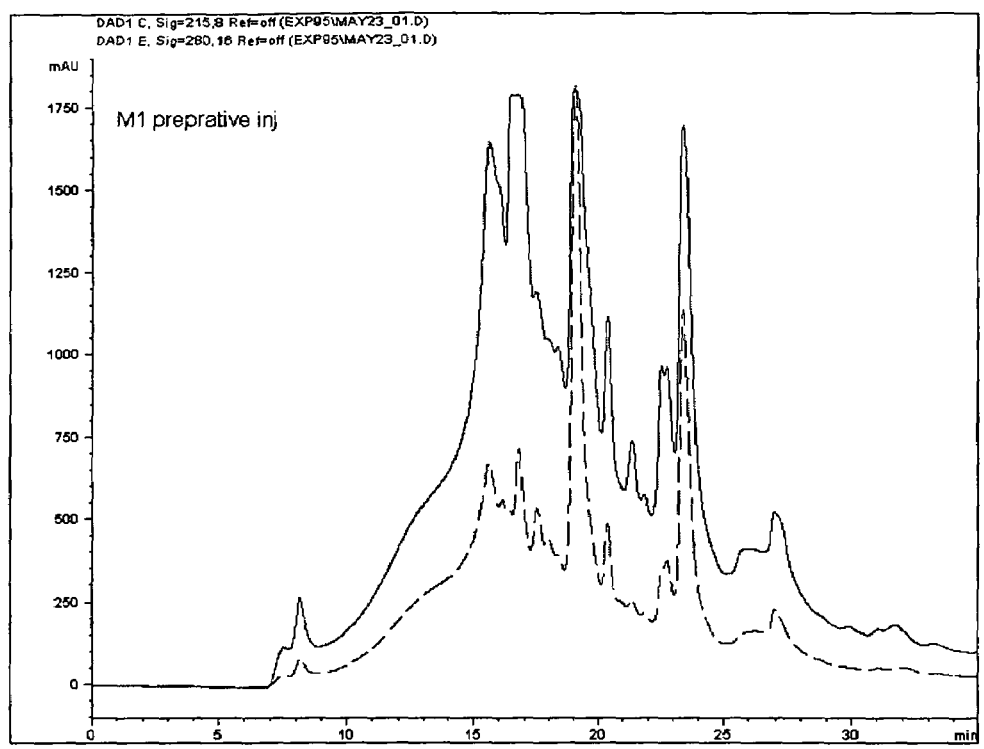
FIG. 9 shows a size-exclusion HPLC chromatogram for the M1 fraction.
Figure 10:
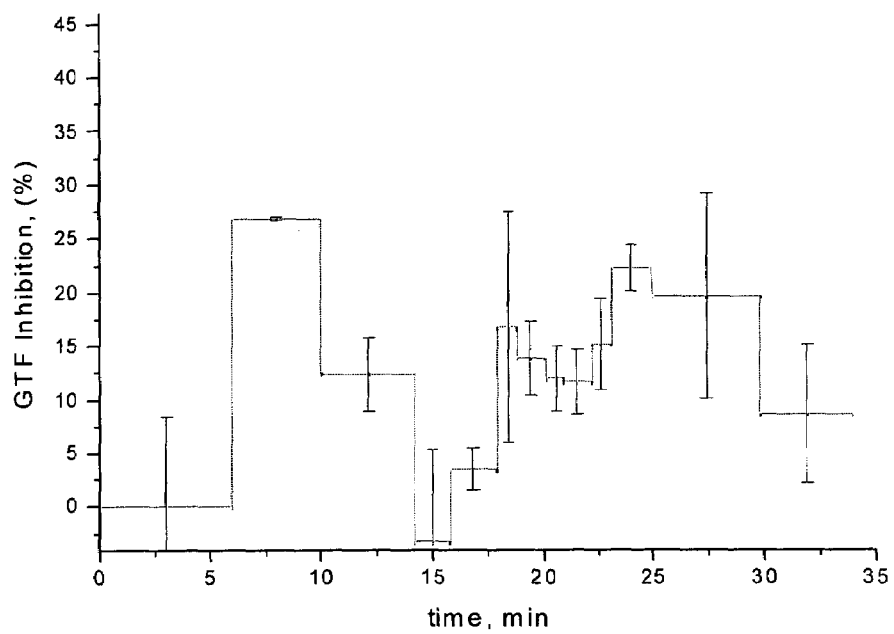
FIG. 10 shows GTF inhibitory activity for the constituents of fraction M1. M1 was fractionated by Size-Exclusive Chromatography. The GTF inhibitory activity is depicted for each collected fraction which is designated according to the time of elution, in minutes (X-axis).

The constituents of the M1 were fractionated by size-exclusive HPLC and their anti-GTF activity was determined. The HPLC profile is shown in FIG. 9, and the GTF inhibitory activity of each fraction is shown in FIG. 10. Each fraction resulting from the chromatography step is designated by the time of elution, in minutes (x-axis). Inhibition of GTF activity is demonstrated in fractions which exhibit high molecular weight components (≧400 kDa). Other fractions which demonstrate GTF inhibitory activity have components with molecular weights below 30 kDa.

Figure 11:
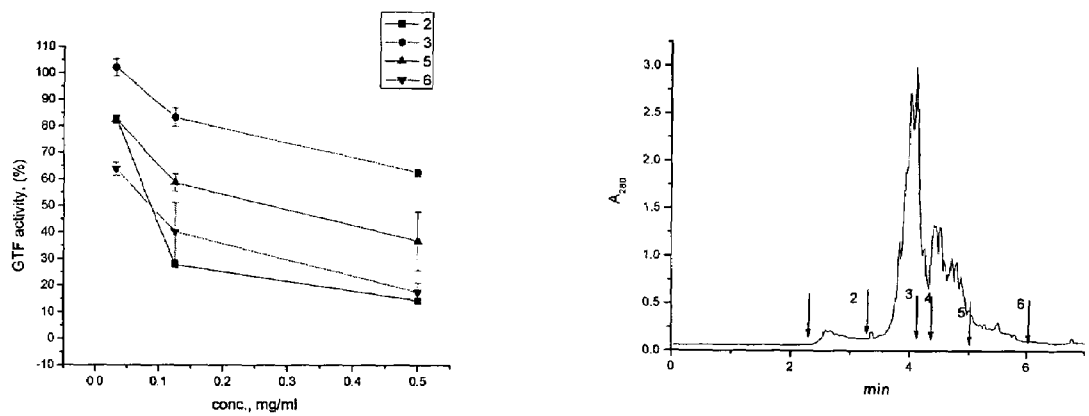
FIG. 11 shows a reverse phase HPLC separation for the MD1 fraction. The GTF inhibitory activity for individual samples obtained during chromatography of the MD1 fraction is also presented.

The MD1 fraction was separated by reverse phase HPLC, individual samples were collected at the times indicated by the arrows on the chromatogram as shown in FIG. 11. The GTF inhibitory activity was determined for several samples. These results are also shown in FIG. 11. The highest GTF inhibitory activity in the MD1 fraction is exhibited by both non-retained polar compounds (fraction #2) and more hydrophobic compounds (fraction #6).

Size-exclusive HPLC of *Mentha* preparations of the present invention has allowed the resolution and identification of distinct components within the inventive Labiatae preparations which demonstrate GTF inhibition. The fractions which exhibit the highest GTF inhibitory activity are those comprised of high molecular weight constituents (≧400 kDa) and also fractions comprised of low molecular weight constituents. Further, in-depth analyses of the composition of the high molecular weight fraction or low molecular weight fraction provides further characterization of the inventive Labiatae preparations which demonstrate anti-GTF activity.

Analysis of the composition of high molecular weight fraction shows a high polysaccharide content (75%), and polyphenolic content below 20% (Table 2, Sample 27). It can be suggested that high molecular weight inhibitors in the *Mentha* extract are polysaccharides, polyphenolic compounds and/or their conjugates.

As Labiatae preparations are demonstrated to comprise low molecular weight inhibitors of GTF, the constituents of the low molecular weight fractions from size-exclusive HPLC were analyzed to identify the individual compounds present in the low molecular weight fractions of the inventive Labiatae preparations. To determine the individual constituents of the low molecular weight fractions, the M2 fraction was used for the analysis and is exemplary of the low molecular weight constituents found in the inventive water dispersible preparations of Labiatae plant extracts. Low molecular weight constituents were analyzed using High Performance Liquid Chromatography—Negative Electrospray Ionization—Ion Trap Mass Spectroscopy. The sample (10 µl, c=3 mg/ml) was injected on Hypersil Gold® C18 column (100× 2.1 mm; 5 µm) and separated using a gradient of mobile phase "B" (acetonitrile+formic acid 0.1%) in mobile phase "A" (5% of acetonitrile in water+0.1% formic acid).

LTQ was set to operate in data-dependent mode using X Calibur software. The Total Ion Current Chromatogram is shown in FIG. 12. The structure of the detected compounds was elucidated based on their MS data, retention time, comparing with standards and or literature data.

Low molecular weight phenolic compounds are understood to inhibit GTF. These phenolic compounds include derivatives from oolong tea (Matsumoto, et al. (2003) "*Molecular analysis of the inhibitory effects of oolong tea polyphenols on glucan-binding domain of recombinant glucosyltransferases from Streptococcus mutans MT8148*", FEMS Microbiol Lett. November 7, 228(1):73-80) and tea polyphenols, as described in Hara, et al., including epicatechin gallate, gallocatechin gallate, epigallocatechin gallate, free theaflavin, theaflavin monogallate A, theaflavin monogallante B and theaflavin digallate. Other GTF inhibitors include the widely distributed flavonoid, apigenin (Koo, et al. (2002) "*Effects of apigenin and tt-farnesol on glucosyltransferase activity, biofilm viability and caries development in rats.*" Oral Microbiol Immunol. December; 17(6):337-43), as well as apple tannins and catechin derivatives from Rosaceae fruits (Tanabe, et al., U.S. Pat. No. 5,994,413).

The results of LC-MS analysis (FIG. 12) of the low molecular weight constituents of the inventive *Mentha* preparations demonstrate that the phenolic compounds previously described as exhibiting GTF inhibition, are not present in a detectable amount in the Labiatae preparations of this invention.

EXAMPLE 7

Inhibition of Plaque Formation by *Mentha* Preparations.

Figure 13:
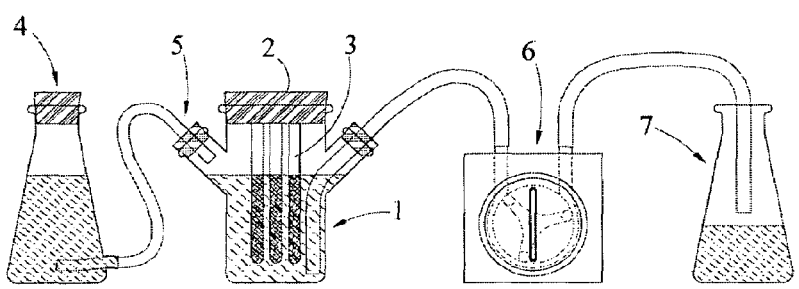
FIG. 13 shows the system used for the determination of the effect of fraction M1 on the inhibition of plaque formation.

The effect of the "M1" fraction on inhibition of plaque formation was investigated using a glass rod model. The system depicted in FIG. 13 was used in these experiments.

Two of these systems were run simultaneously in parallel (control and inhibitor), as described below.

Todd-Hewitt Broth ("THB"), a general-purpose medium which is primarily used for the cultivation of beta-hemolytic streptococci, was obtained from Bacto®. THB (30 g) was dissolved in 1 L of deionized water. A portion of the obtained THB media (200 mL) was placed in a flask, autoclaved, cooled down to room temperature and a sterile solution of glucose (2 mL; 50% w/v) was then aseptically added. This is a growth media (0.5% glucose in 3% THB).

Powdered sucrose (16 g) was added to the rest of THB media (800 mL) and the media was autoclaved. This is an incubation media (2% sucrose in 3% THB).

The "M1" fraction was dissolved in growth media and incubation media to achieve concentration 1 mg/mL; obtained media were subjected to sterilizing by filtration.

A stock media containing *Streptococcus mutans* strain 6715-64C (0.2 mL) was aseptically added to a vial containing 4 mL of growth media, bacteria were grown overnight in anaerobic conditions (10% $CO_2$, 10% $H_2$, balance by $N_2$) at 37° C.

Eight glass rods were pre-weighed and inserted in two pre-punched rubber corks. The two reaction vessels were hermetically assembled and autoclaved alongside with media reservoirs. The reaction vessels were cooled down to room temperature and aseptically charged with 75 mL of growth media, with M1 (Inhibited) or without inhibitor (Control). The apparatus' were placed in a temperature controlled room and equilibrated to 37° C. Then, each of the vessels was inoculated with 1 mL of the overnight grown culture of *Streptococcus mutans*. After 2 hours of incubation, a sterile needle equipped with sterile disposable filter was inserted through the side rubber cork to prevent airlock formation, and the vessel's contents were pumped out. The filters were removed, capillary outlets from reservoirs containing the corresponding incubation media (with M1 or without inhibitor) were connected to the needle and reservoirs were uplifted to charge vessels with new media to the initial level.

Figure 14:
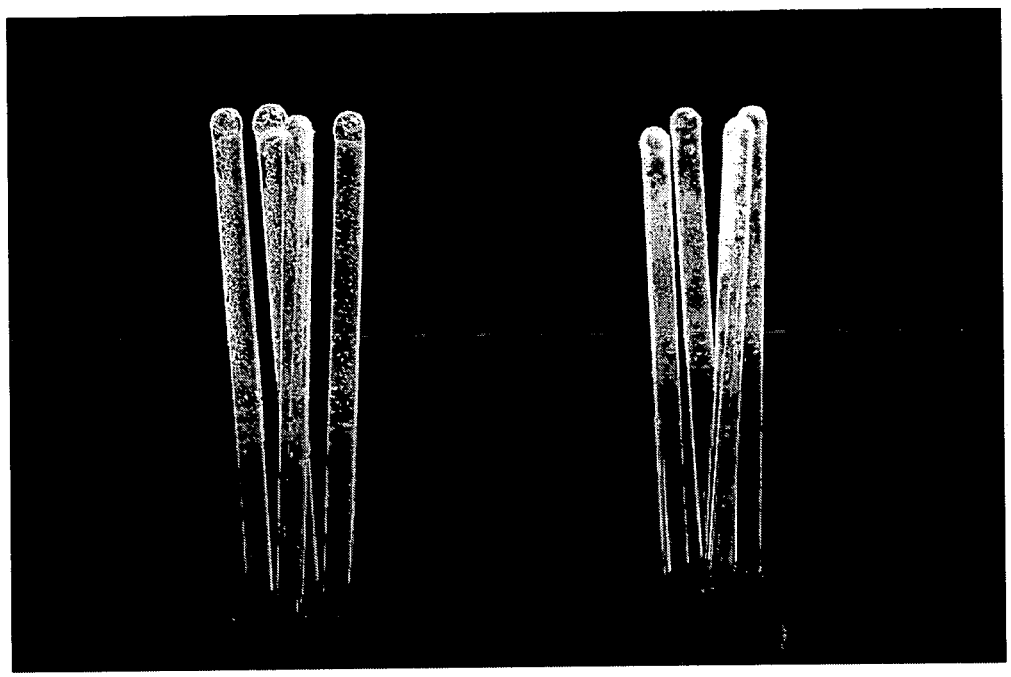
FIG. 14 shows plaque accumulation in cultures comprising fraction M1 (Inhibited) vs. Control as described in Example 7.
Figure 15:
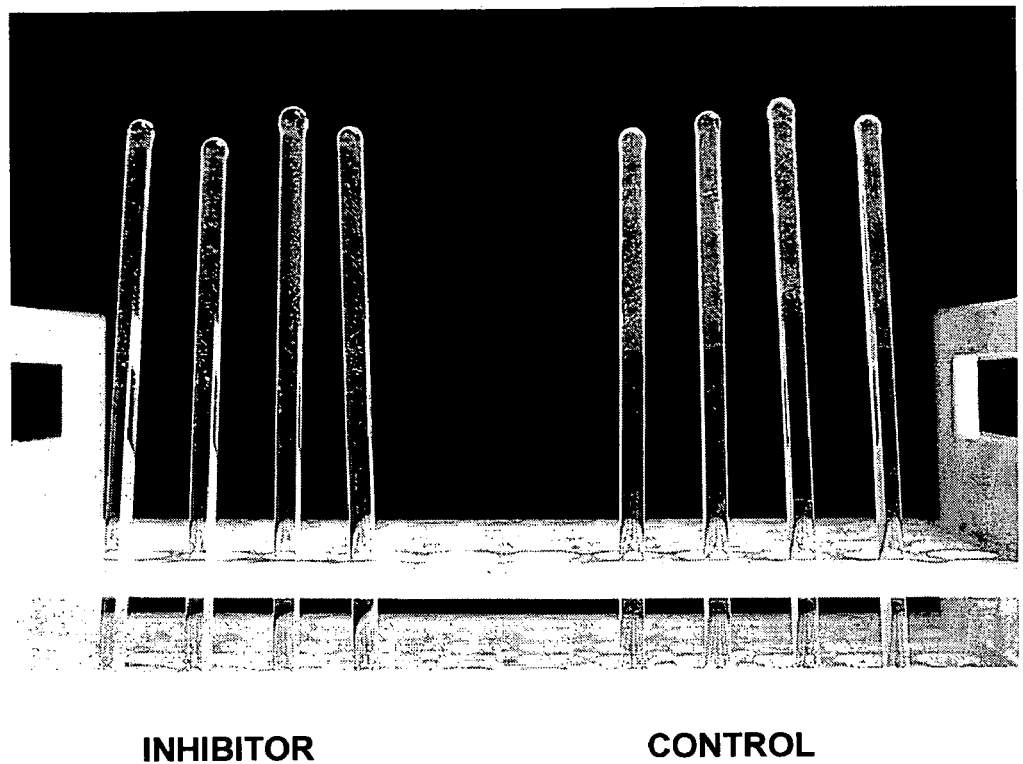
FIG. 15 shows plaque accumulation in cultures comprising fraction M1 (Inhibited) vs. Control after drying at 80° C. overnight, as described in Example 7.

After 6 hours of incubation, a partial media exchange was completed by pumping out the 30 mL of the incubation media and simultaneously replacing it with fresh media from the connected reservoirs. The systems were left for another 18 hours at 37° C. (total incubation time was 24 hours). After incubation was completed, the apparatus was disassembled, the rods (still inserted in cocks) were gently immersed three times in distilled water to remove tenuously adsorbed ("fluffy") plaque, and the rods were photographed (FIG. 14). Then the rods were dried overnight at 80° C. and weighed to measure the amount of the accumulated plaque. The dried rods, arranged in a row, were also photographed (FIG. 15). The weight of the accumulated plaque on each rod is shown in Table 4.

TABLE 4

Amounts of accumulated plaque (in milligrams)

| Rod # | Control | Inhibitor |
|---|---|---|
| 1 | 6 | 2 |
| 2 | 4 | 3 |
| 3 | 4 | 3 |
| 4 | 5 | 2 |
| Average | 4.75 | 2.5 |
| STDEV | 0.957 | 0.577 |
| Plaque formation (%) | 100 | 53 |
| RSTDEV (%) | 20 | 12 |

Media from "M1" treated (Inhibitor) and Control samples were diluted ten times and the optical density at 590 nm was taken. Reported values were almost identical, which confirms the same number of bacterial counts in the samples. Therefore, the inhibition of the plaque formation is not due to bacteriocidal properties of M1, but through the inhibition of GTF and the inhibition of adhesion.

EXAMPLE 8

Effect of *Mentha* Preparations on Remineralization—Calcium Phosphate Mineralization Study.

The following stock solutions were prepared. In order to achieve maximum dissolution, solutions A-D were stirred for 4 hours at 24° C. The solutions were then centrifuged at 4° C. for 20 min at 10,000×g to remove particulate matter.

Stock Solutions:

| | |
|---|---|
| Solution A | 10 ml 0 mg/ml Pepticase (Sigma, P1192-250G, batch 030K0223) in deionized distilled water (DDW) |
| Solution B | 10 ml 10 mg/ml BSA (Sigma, A2153, lot 46H0629) in DDW |
| Solution C | 10 ml 10 mg/ml "M" in DDW |
| Solution D | 10 ml 10 mg/ml "M1" in DDW |
| Solution E | 500 ml 100 mM $CaCl_2$ in DDW |
| Solution F | 500 ml 100 mM $(NH_4)_2HPO_4$ in DDW |

3 N HCl
3 N $NH_4OH$

The solutions A-D were diluted in DDW to the concentration 1 mg/mL, the solutions E and F then were added to the samples to establish final concentrations of 1 and 1.67 mM for phosphate and calcium, respectively. In the control, sample solutions E and F were mixed to establish final concentrations of 1 and 1.67 mM for phosphate and calcium, respectively, without adding any additives. The pH of the solutions was adjusted to pH 8.

List of Samples:

| | |
|---|---|
| A | 1 mg/mL of solution A, 1 mM $(NH_4)_2HPO_4$ and 1.67 mM $CaCl_2$. |
| B | 1 mg/mL of solution B, 1 mM $(NH_4)_2HPO_4$ and 1.67 mM $CaCl_2$. |
| C | 1 mg/mL of solution C, 1 mM $(NH_4)_2HPO_4$ and 1.67 mM $CaCl_2$. |
| D | 1 mg/mL of solution D, 1 mM $(NH_4)_2HPO_4$ and 1.67 mM $CaCl_2$. |
| Control | 1 mM $(NH_4)_2HPO_4$ and 1.67 mM $CaCl_2$. |

2 ml aliquots of each sample were obtained at 2 hours, 1 day, 2 days, 3 days and 7 days after the beginning of mineralization experiments. The aliquots were centrifuged at 20,000×g for 20 min. Supernatant was then analyzed by atomic adsorption spectroscopy in order to assess the concentration of calcium remaining in solution. Pellets were submitted for electron diffraction analysis.

Atomic Adsorption Analysis (AAA)

AAA was used to assess the changes in calcium concentration in the solution during the mineralization experiments. The changes in the amount of calcium in solution are directly related to the amount of mineral formed. Its relations can be described by the following equation: $M_{Ca}^{Sol}=M_{Ca}^{ini}-M_{Ca}^{min}$; where $M_{Ca}^{ini}$ is the amount of calcium in the sample at the beginning of the experiment; $M_{Ca}^{Sol}$ is the amount of calcium in solution at certain time point; $M_{Ca}^{min}$ is the amount of calcium in the precipitate at certain time point.

The standard curve was created using a series of $CaCl_2$ solutions made from a 1,000 ppm calcium reference solution (Fisher). The correlation coefficient (r) of the standard curve with a theoretical model was 0.98. Three 0.5 sec long consecutive measurements were performed on each standard and experimental solution. The accuracy of the measurements is 2% or better.

Figure 16:
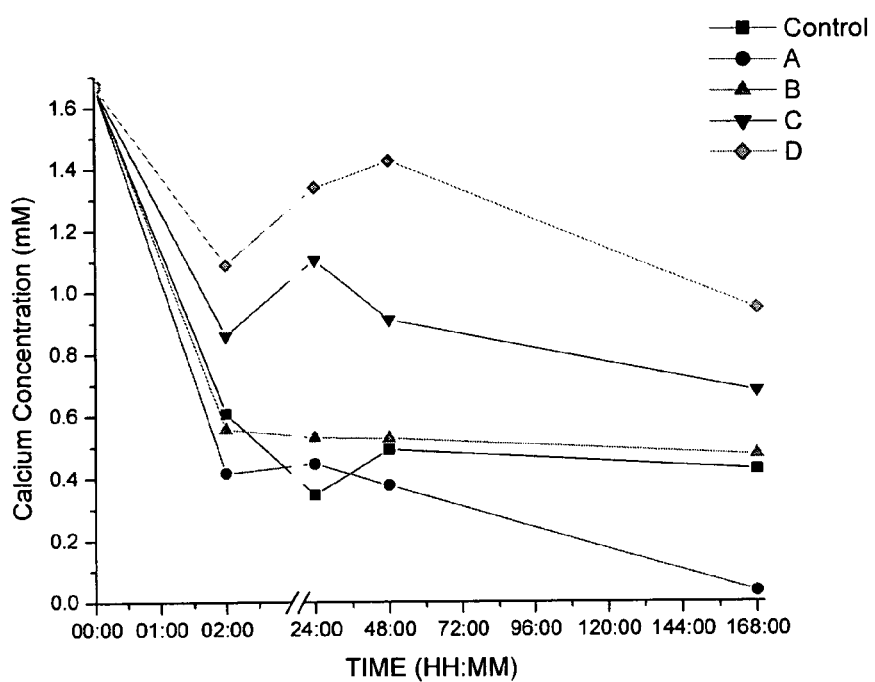
FIG. 16 shows changes in the calcium concentrations in mineralization solutions during the experiments described in Example 8.

The results of AAA are presented in Table 5 and FIG. 16. The data suggests that BSA did not significantly affect the kinetics of the mineralization reaction. The calcium concentration changes in the presence of BSA closely followed the control, except at the 24 hour time point. At this time point, the concentration of calcium in the control solution transiently dropped to 0.35 mM (Table 5; FIG. 16), which suggested an increased mineral precipitation. At the same time, the calcium concentration in the solution containing BSA remained virtually unchanged, which can be attributed to the buffering capacity of BSA. The AAA data showed that Pepticase stimulated spontaneous mineral precipitation and shifted the equilibrium towards formation of a mineral phase (Table 5, FIG. 16).

TABLE 5

Calcium concentrations (mM) in the mineralization solutions

| TIME | Control | A | B | C | D |
|---|---|---|---|---|---|
| start | 1.67 | 1.67 | 1.67 | 1.67 | 1.67 |
| 2 hours | 0.608 | 0.416 | 0.557 | 0.86 | 1.09 |
| 1 day | 0.346 | 0.445 | 0.529 | 1.105 | 1.336 |
| 2 days | 0.491 | 0.376 | 0.527 | 0.91 | 1.425 |
| 7 days | 0.427 | 0.036 | 0.474 | 0.68 | 0.948 |

The presence of either "M" or "M1" compounds in the reaction prevented spontaneous mineral precipitation; however, "M1" was a much more potent inhibitor than "M" (Table 5, FIG. 16).

Electron Diffraction Analysis of Mineral Precipitates

Electron diffraction studies showed that 2 days after the beginning of the reaction, in the control and in sample B, a crystalline mineral formed, whereas in samples A, C, and D, amorphous mineral precipitates were formed. By day 7, the mineral precipitates in all samples transformed into a crystalline mineral phase.

This example demonstrates that "M" and "M1" have a unique ability to stabilize calcium phosphate solutions supersaturated in respect to calcium phosphate mineral phases. This property of the "M" and "M1" compounds may be advantageous for the restoration of caries lesions (Margolis. H. C. and Moreno, E. C. (1993) J. Dent. Res. 71:1776-1784; Margolis, H. C. and Moreno, E. C. (1994) Crit. Rev. Oral Biol. Med. 5:1-25).

"M" and "M1" can transiently stabilize amorphous calcium phosphate (ACP) similarly to casein peptides. Casein peptides are shown to inhibit caries via formation of a metastable ACP phase (Reynolds, E. C. (1997) J. Dent. Res. 76:1587-1595; Reynolds, et. al., (1999) J. Clin. Dent. 10:86-88; Reynolds, et. al., (2003) J. Dent. Res. 82:206-211).

EXAMPLE 9

Anti-Inflammatory Effect of *Mentha* Preparations. Assay for Cyclooxygenase 2 (COX-2) Inhibition.

The enzyme COX-2 is recognized to be a key enzyme in the inflammation cascade and it is a target of action of a number anti-inflammatory drugs. The COX inhibition assay was performed using an Enzymatic Immunoassay (EIA) kit from Cayman Co. according to the manufacturer's instructions. All reactions were carried out in triplicate. The 96-well microplate was read at 405 nm using a Vmax plate reader.

Figure 17:
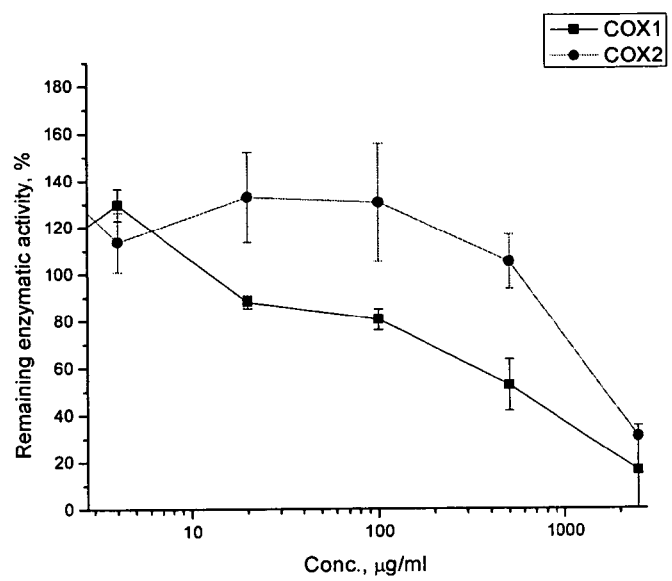
FIG. 17 shows inhibition of cyclooxygenase 2 (COX-2) activity by water dispersible *Mentha* extract "M" preparations which were isolated as described in Example 1.

As shown in FIG. 17, the *Mentha* derived "M" preparations are capable of inhibition of both isoforms of COX enzymes in a dose dependent manner which provides basis for their anti-inflammatory activity.

EXAMPLE 10

The Inhibition of Adhesion of Oral Pathogens to Plaque by Mint Fractions was Demonstrated by Binding to Radioactive Carboxyl-[$^{14}$C]-Dextran (NEN Corporation, S.A.=1.4 μCi/g).

*Streptococcus mutans* (strain 6715), used in the binding experiments, was grown in Brain Heart Infusion (BHI) broth which is a general-purpose liquid medium used in the cultivation of fastidious and nonfastidious microorganisms. Reaction mixtures contained BHI or BHI+0.01% sucrose, $10^9$ washed bacteria and $10^{15}$ molecules of [$^{14}$C]-dextran in 1 mL of phosphate buffered saline (0.02 M, pH 7.5+0.15% NaCl) with or without tested fractions, and were incubated at 37° C. with continuous shaking for 1 hour. Pelleted bacteria were washed four times in buffer, solubilized with 0.25 M NaOH, placed in BioSolv® (Beckman) and counted in a liquid scintillation spectrometer.

Figure 18:
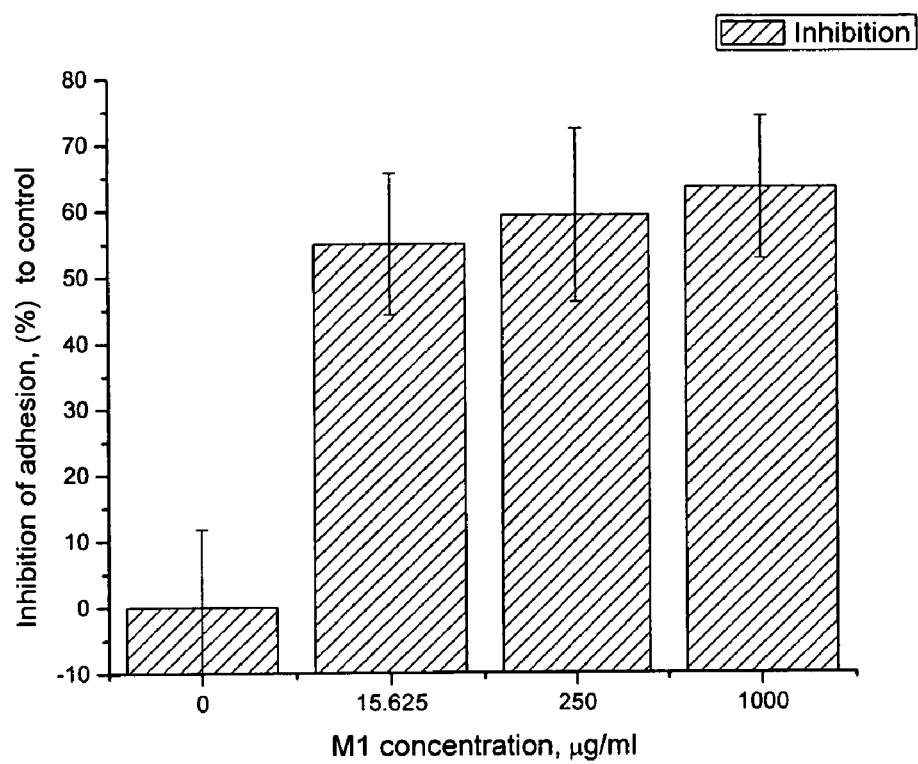
FIG. 18 shows inhibition of adhesion of *Streptococcus mutans* to Dextran by fraction M1.

As shown in FIG. 18, the "M1" preparation showed strong inhibition of adhesion of *S. mutans* to the Dextran.

CONCLUSIONS

The instant experimentation demonstrates that novel water dispersible extract preparations of Labiatae plant material can be prepared from a variety of sources. These extracts are demonstrated to be free of typical Labiatae extract components, including essential oil components. The unique composition of these fractions was demonstrated to possess significant beneficial oral care properties including, but not limited to prevention of dental caries through suppression of plaque formation and deposition via inhibition of glucosyltransferase enzyme activity and through prevention of caries-associated inflammation by cyclooxygenase inhibition.

The high activities of the object of the invention and compositions thereof, as evidenced by the tests reported, is indicative of utility based on its valuable activity in human beings as well as in domesticated animals, particularly dogs and cats.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

We claim:

1. A water dispersible extract preparation of *Mentha piperita* plant material comprising between about 20-25% of a polysaccharide component and between about 6-8% of a polyphenol component of the total mass.

2. The water dispersible extract preparation of claim 1, in which the preparation is free of essential oil components.

3. The water dispersible extract preparation of claim 2, in which the preparation is free of thymol, menthol, and/or carvacrol components.

4. The water dispersible extract preparation of claim 1, wherein the *Mentha piperita* plant material is derived from spent mint hay.

5. The water dispersible extract preparation of claim 4, wherein the *Mentha piperita* plant material is derived from spent mint hay which is dried.

6. The water dispersible extract preparation of claim 1, further comprising extracts, fractions, and compounds possessing beneficial oral care properties including inhibitory activity towards to glucosyltransferases, remineralization properties, anti-adhesion activity, inhibitory activity towards cyclooxygenases and lipoxygenases, anti-oxidant properties, and/or anti-inflammatory properties.

7. A method of providing oral care benefits in a living animal, including a human, by means of inhibiting glucosyltransferases, inhibiting adhesion of oral pathogens and/or providing a remineralization effect, comprising the step of administering to the oral cavity of a living animal, including a human, an amount of a water dispersible extract preparation of claim 1 which is effective to provide an oral care benefit.

8. The method of claim 7, wherein the water dispersible extract preparation is selected for its inhibitory activity towards glucosyltransferases, anti-adhesion activity, remineralization properties and/or anti-inflammatory properties.

9. The method of claim 7, wherein the water dispersible extract preparation is contacted with the oral cavity in the form of a chewing gum, a breath freshening strip, a confectionary product, a food product, a beverage, a toothpaste, a dentifrice, a mouthwash, a rinse, a floss, a pet food, a pet snack, or a pet chewing material, selected from pig's ears and raw hides.

10. The method of claim 9, wherein the beneficial effect of the water dispersible extract preparation may be further enhanced by incorporation of extracts, fractions, and compounds possessing beneficial oral care properties including inhibitory activity towards to glucosyltransferases, anti-microbial activity against oral pathogens, remineralization properties, anti-adhesion activity, inhibitory activity towards cyclooxygenases and lipoxygenases, breath freshening properties, anti-oxidant properties, and/or anti-inflammatory properties.

11. A method of providing a remineralization effect in a living animal, including a human comprising the step of administering to the oral cavity of a living animal, including a human, an amount of a water dispersible extract preparation of claim 1 which is effective to provide a remineralization effect.

* * * * *